(12) United States Patent
Habeck et al.

(10) Patent No.: US 6,436,373 B1
(45) Date of Patent: Aug. 20, 2002

(54) OLIGOMERIC DIARYLBUTADIENES

(75) Inventors: Thorsten Habeck, Meckenheim; Thomas Wünsch, Speyer; Horst Westenfelder, Nuestadt, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/455,484

(22) Filed: Dec. 6, 1999

(30) Foreign Application Priority Data

Dec. 11, 1998 (DE) .......................................... 198 57 127

(51) Int. Cl.[7] .................................................. A61K 7/42
(52) U.S. Cl. ...................... 424/59; 424/401; 558/308; 560/1
(58) Field of Search .................... 424/401, 59; 558/303; 560/1

(56) References Cited

U.S. PATENT DOCUMENTS 6,238,649 B1 * 5/2001 Habeck et al. ................. 424/59

FOREIGN PATENT DOCUMENTS

| JP | 07 017912 | 1/1995 |
| WO | WO 91/11989 | 8/1991 |
| WO | WO 96/15102 | 5/1996 |

* cited by examiner

Primary Examiner—Jose' G. Dees
Assistant Examiner—Konata M George
(74) Attorney, Agent, or Firm—Keil & Weinkauf

(57) ABSTRACT

Oligomeric 4,4-diarylbutadienecarboxylates and -carboxamides of the formula I $$\left[ \begin{array}{c} (R^1)_n\text{-Ar} \\ (R^2)_n\text{-Ar} \end{array} \hspace{-2pt} C\!=\!CH\!-\!CH\!=\!C \hspace{-2pt} \begin{array}{c} O \\ \| \\ C\!-\!Y \\ R^3 \end{array} \right]_m \hspace{-4pt} X, \quad I$$

in which $R^1$ and $R^2$ independently of one another are hydrogen, an aliphatic, cycloaliphatic, aromatic, araliphatic or heterocyclic radical or substituents which confer solubility in water, chosen from the group consisting of carboxylate, sulfonate or ammonium radicals;

$R^3$ is an aliphatic, cycloaliphatic, aromatic, araliphatic or heterocyclic radical or a radical which is bonded by a carbonyl, sulfonyl or a phosphonyl group, or is a carboxylate or a cyano group;

Y is the group;

$$-\!\text{O}\!-\quad \text{or} \quad -\!\underset{\underset{R^4}{|}}{\text{N}}\!-,$$

in which $R^4$ is hydrogen, an aliphatic, cycloaliphatic, aromatic, araliphatic or heterocyclic radical and m is from 2 to 10, n is from 1 to 3, and x is the m-valent radical of a polyol having from 2 to 10 hydroxyl groups.

6 Claims, No Drawings

OLIGOMERIC DIARYLBUTADIENES

The present invention relates to novel oligomeric 4,4-diarylbutadienecarboxylates and -carboxamides and their use as sunscreens and also to a process for their preparation.

The sunscreens employed in cosmetic and pharmaceutical preparations have the task of preventing, or at least diminishing the consequences of, harmful effects of sunlight on the human skin. However, these sunscreens also serve to protect other ingredients from decomposition or breakdown by UV radiation. In hair cosmetic formulations the aim is to reduce damage to the keratin fibers by UV rays.

The sunlight reaching the surface of the earth contains UV-B radiation (280 to 320 nm) and UV-A radiation (>320 nm), which are directly adjacent to the visible light region. The effect on the human skin is manifested, particularly in the case of UV-B radiation, by sunburn. Accordingly, the industry offers a relatively large number of substances which absorb UV-B radiation and thus prevent sunburn.

Dermatological investigations have now shown that UV-A radiation is also perfectly capable of causing skin damage and allergies by, for example, damaging the keratin or elastin. This reduces the elasticity and water storage capacity of the skin, i.e. the skin becomes less supple and tends to form wrinkles. The noticeably high incidence of skin cancer in regions where the sun's radiation is strong shows that damage to the genetic information in the cells is evidently also caused by sunlight, specifically by UV-A radiation. All these findings therefore make it appear necessary to develop efficient filter substances for the UV-A region.

There is a growing demand for sunscreens for cosmetic and pharmaceutical preparations which can be used in particular as UV-A filters and whose absorption maxima ought therefore to be in the range from about 320 to 380 nm. In order to achieve the required effect by using the minimum amount, sunscreens of this type ought additionally to have a highly specific absorbance. Sunscreens for cosmetic preparations must also meet a large number of other requirements, for example good solubility in cosmetic oils, high stability of the emulsions produced with them, toxicological acceptability, and slight intrinsic odor and slight intrinsic color.

Another requirement which sunscreens must meet is adequate photostability. However, this is only inadequately ensured, if at all, with the UV-A-absorbing sunscreens hitherto available.

French Patent No. 2 440 933 describes 4-(1,1-dimethylethyl)-4'-methoxydibenzoylmethane as a UV-A filter. It is proposed to combine this specific UV-A filter, which is sold by GIVAUDAN under the name "PARSOL 1789", with various UV-B filters in order to absorb all UV rays having a wavelength from 280 to 380 nm.

However, this UV-A filter does not have sufficient photochemical stability, when used alone or in combination with UV-B filters, to ensure sustained protection of the skin during sunbathing for prolonged periods, which means that repeated applications at regular and frequent intervals are required if effective protection of the skin from all UV rays is desired.

For this reason, EP-A-0 514 491 discloses the stabilization of the insufficiently photostable UV-A filters by adding 2-cyano-3,3-diphenylacrylic esters which themselves act as filters in the UV-B region.

It has furthermore already been proposed in EP-A-0 251 398 to combine chromophores absorbing UV-A radiation and UV-B radiation into one molecule by using a linker. This has the disadvantage that, firstly a free combination of UV-A and UV-B filters in the cosmetic preparation is no longer possible, and that difficulties in the chemical linkage of the chromophores allow only certain combinations.

U.S. Pat. No. 4,950,467 describes the use of 2,4-pentadienoic acid derivatives as UV absorbers in cosmetic preparations. The monoaryl-substituted compounds specified as being preferred in this patent also have the disadvantage that they have inadequate photostability.

It is an object of the present invention to propose sunscreens for cosmetic and pharmaceutical purposes which absorb in the UV-A region with high absorbance, are photostable, have a low intrinsic coloration, i.e. a sharp band structure, and, depending on the substituents, are soluble in oil or water.

The object was essentially achieved in the previously unpublished DE-A 19755649 (O.Z. 48641) with monomeric 4,4-diarylbutadienes which are functionalized in the 1-position, with the limitation that the object still existed to find sunscreens which, in addition to said properties, have low skin penetration.

We have found that this object is achieved according to the invention with novel oligomeric 4,4-diarylbutadienecarboxylates or -carboxamides of the formula I

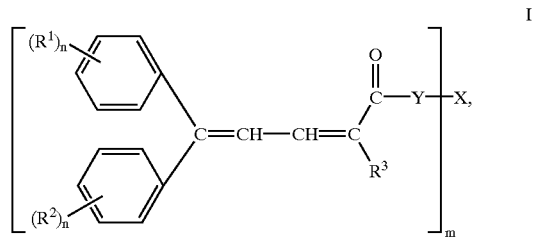

in which

R$^1$ and R$^2$ independently of one another are hydrogen, an aliphatic, cycloaliphatic, aromatic, araliphatic or heterocyclic radical or substituents which confer solubility in water, chosen from the group consisting of carboxylate, sulfonate or ammonium radicals;

R$^3$ is an aliphatic, cycloaliphatic, aromatic, araliphatic or heterocyclic radical or a radical which is bonded by a carbonyl, sulfonyl or a phosphonyl group, or is a carboxylate or a cyano group;

Y is the group

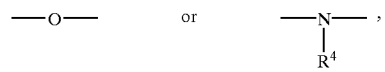

in which

R$^4$ is hydrogen, an aliphatic, cycloaliphatic, aromatic, araliphatic or heterocyclic radical and m is from 2 to 10, n is from 1 to 3, and x is the m-valent radical of a polyol having from 2 to 10 hydroxyl groups.

In particular, the variables are defined as follows:

R$^1$ and R$^2$ are hydrogen, C$_1$–C$_{20}$-alkyl, C$_2$–C$_{10}$-alkenyl, C$_3$–C$_{10}$-cycloalkyl, C$_3$–C$_{10}$-cycloalkenyl, C$_1$–C$_{12}$-alkoxy, C$_1$–C$_{20}$-alkoxycarbonyl, C$_1$–C$_{12}$-alkylamino, C$_1$–C$_{12}$-dialkylamino, aryl, heteroaryl, optionally substituted, substituents which confer solubility in water, chosen from the group consisting of carboxylate, sulfonate or ammonium radicals;

$R^3$ is hydrogen, $COOR^5$, $COR^5$, $CONR^5R^6$, CN, $O=S(-R^5)=O$, $O=S(-OR^5)=O$, $R^7O-P(-OR^8)=O$, $C_1-C_{20}$-alkyl, $C_2-C_{10}$-alkenyl, $C_3-C_{10}$-cycloalkyl, $C_7-C_{10}$-bicycloalkyl, $C_3-C_{10}$-cycloalkenyl, $C_7-C_{10}$-bicycloalkenyl, aryl, heteroaryl, optionally substituted;

$R^4$ to $R^8$ are hydrogen, $C_1-C_{20}$-alkyl, $C_2-C_{10}$-alkenyl, $C_3-C_{10}$-cycloalkyl, $C_7-C_{10}$-bicycloalkyl, $C_3-C_{10}$-cycloalkenyl, $C_7-C_{10}$-bicycloalkenyl, aryl, heteroaryl, each optionally substituted;

it being possible for the variables $R^5$ to $R^8$ to form with each other, in each case together with the atoms to which they are bonded, a common 5- or 6-membered ring.

Alkyl radicals $R^1$ to $R^8$ which may be mentioned are branched or unbranched $C_1-C_{20}$-alkyl chains, preferably methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl or n-eicosyl.

Alkenyl radicals $R^1$ to $R^8$ which may be mentioned are branched or unbranched $C_2-C_{10}$-alkenyl chains, preferably vinyl, propenyl, isopropenyl, 1-butenyl, 2-butenyl, 1-pentenyl, 2-pentenyl, 2-methyl-1-butenyl, 2-methyl-2-butenyl, 3-methyl-1-butenyl, 1-hexenyl, 2-hexenyl, 1-heptenyl, 2-heptenyl, 1-octenyl or 2-octenyl.

Cycloalkyl radicals which may be mentioned for $R^1$ to $R^8$ are preferably branched or unbranched $C_3-C_{10}$-cycloalkyl chains, such as cyclopropyl, cyclobutyl, cyclopentyl, cyclohexyl, cycloheptyl, 1-methylcyclopropyl, 1-ethylcyclopropyl, 1-propylcyclopropyl, 1-butylcyclopropyl, 1-pentylcyclopropyl, 1-methyl-1-butylcyclopropyl, 1,2-dimethylcyclopropyl, 1-methyl-2-ethylcyclopropyl, cyclooctyl, cyclononyl or cyclodecyl.

Cycloalkenyl radicals which may be mentioned for $R^1$ to $R^8$ are preferably branched or unbranched $C_3-C_{10}$-cycloalkenyl chains having one or more double bonds such as cyclopropenyl, cyclobutenyl, cyclopentenyl, cyclopentadienyl, cyclohexenyl, 1,3-cyclohexadienyl, 1,4-cyclohexadienyl, cycloheptenyl, cycloheptatrienyl, cyclooctenyl, 1,5-cyclooctadienyl, cyclooctatetraenyl, cyclononenyl or cyclodecyl.

The cycloalkenyl and cycloalkyl radicals can optionally be substituted by one or more, e.g. from 1 to 3, radicals such as halogen, e.g. fluorine, chlorine or bromine, cyano, nitro, amino, $C_1-C_4$-alkylamino, $C_1-C_4$-dialkylamino, hydroxyl, $C_1-C_4$-alkyl, $C_1-C_4$-alkoxy or other radicals, or may contain from 1 to 3 heteroatoms such as sulfur, nitrogen, whose free valences may be saturated by hydrogen or $C_1-C_4$-alkyl, or oxygen in the ring.

Bicycloalkyl or bicycloalkenyl radicals which may be mentioned for $R^3$ to $R^8$ are saturated or unsaturated $C_7-C_{10}$ bicyclic ring systems, in particular bicyclic terpenes such as pinane, pinene, bornane, camphor derivatives or also adamantane.

Suitable alkoxy radicals $R^1$ and $R^2$ are those having from 1 to 12 carbon atoms, preferably having from 1 to 8 carbon atoms.

Examples include:

| | |
|---|---|
| methoxy | ethoxy |
| isopropoxy | n-propoxy |
| 1-methylpropoxy | n-butoxy |
| n-pentoxy | 2-methylpropoxy |
| 3-methylbutoxy | 1,1-dimethylpropoxy |
| 2,2-dimethylpropoxy | hexoxy |
| 1-methyl-1-ethylpropxy | heptoxy |
| octoxy | 2-ethylhexoxy |

Alkoxycarbonyl radicals $R^1$ and $R^2$ are, for example, esters which contain the abovementioned alkoxy radicals or radicals of higher alcohols, e.g. having up to 20 carbon atoms, such as iso-$C_{15}$-alcohol.

Suitable mono- or dialkylamino radicals $R^1$ and $R^2$ are those which contain alkyl radicals having from 1 to 12 carbon atoms, for example methyl, n-propyl, n-butyl, 2-methylpropyl, 1,1-dimethylpropyl, hexyl, heptyl, 2-ethylhexyl, isopropyl, 1-methylpropyl, n-pentyl, 3-methylbutyl, 2,2-dimethylpropyl, 1-methyl-1-ethylpropyl and octyl.

Aryl is taken to mean aromatic rings or ring systems having from 6 to 18 carbon atoms in the ring system, for example phenyl or naphthyl, which can be optionally substituted by one or more radicals such as halogen, e.g. fluorine, chlorine or bromine, cyano, nitro, amino, $C_1-C_4$-alkylamino, $C_1-C_4$-dialkylamino, hydroxyl, $C_1-C_4$-alkyl, $C_1-C_4$-alkoxy or other radicals. Preference is given to optionally substituted phenyl, methoxyphenyl and naphthyl.

Heteroaryl radicals are advantageously single or fused aromatic ring systems having one or more heteroaromatic 3- to 7-membered rings. The heteroatoms which may be present are one or more nitrogen, sulfur and/or oxygen atoms in the ring or in the ring system.

Hydrophilic radicals, i.e. those which make the compounds of the formula I soluble in water, for $R^1$ and $R^2$ are, for example, carboxyl and sulfoxy radicals and in particular salts thereof with any physiologically compatible cations, such as the alkali metal salts or such as the trialkylammonium salts, such as tri(hydroxyalkyl)ammonium salts or the 2-methylpropan-1-ol-2-ammonium salts. In addition, ammonium, in particular alkylammonium radicals with any physiologically compatible anions are suitable.

Preference is given to compounds of the formula I in which $R^1$ and $R^2$ independently of one another are hydrogen, $C_1-C_{12}$-alkyl, $C_1-C_8$-alkoxy, $C_1-C_{12}$-alkylamino, $C_1-C_{12}$-dialkylamino, substituents which confer solubility in water, chosen from the group consisting of carboxylate, sulfonate or ammonium radicals;

$R^3$ is hydrogen, $COOR^5$, $COR^5$, $CONR^5R^6$, CN, $C_1-C_{12}$-alkyl, $C_3-C_6$-cycloalkyl, $C_7-C_{10}$-bicycloalkyl, phenyl, naphthyl, thienyl, optionally substituted;

$R^5$ and $R^6$ independently of one another are hydrogen, $C_1-C_{12}$-alkyl, $C_3-C_6$-cycloalkyl, $C_7-C_{10}$-bicycloalkyl, phenyl, naphthyl, optionally substituted and n is from 1 to 3.

$C_1-C_{12}$-alkyl radicals $R^1$ to $R^6$ which may be mentioned with particular preference are methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 2-ethylhexyl.

Cycloalkyl radicals $R^3$ to $R^6$ which may be mentioned with particular preference are branched or unbranched cyclopentyl and cyclohexyl.

Particularly preferred mono- or dialkylamino radicals $R^1$ and $R^2$ are methyl, ethyl, n-propyl, n-butyl, 2-methylpropyl, 1,1-dimethylpropyl and 2-ethylhexyl.

Bicycloalkyl radicals which may be mentioned with particular preference for $R^3$ to $R^6$ are camphor derivatives.

The substituents $R^1$ and $R^2$ can in each case be bonded in the ortho, meta and/or para position on the aromatic compound. In the case of disubstituted aromatic compounds (n=2), $R^1$ and $R^2$ can be in the ortho/para or meta/para position. Preference is given to compounds of the formula I where n=1 in which $R^1$ is identical to $R^2$ and both radicals are in the para position.

Very particular preference is given to compounds of the formula I in which $R^1$ and $R^2$ independently of one another are hydrogen, $C_1$–$C_{12}$-alkyl, $C_1$–$C_8$-alkoxy, substituents which confer solubility in water, chosen from the group consisting of carboxylate, sulfonate or ammonium radicals;

$R^3$ is hydrogen, $COOR^5$, $COR^5$, $CONR^5R^6$, CN, $C_3$–$C_6$-cycloalkyl or $C_7$–$C_{10}$-bicycloalkyl.

Preference is also given to the use of compounds of the formula I in which $R^1$ and $R^2$ independently of one another are hydrogen, $C_1$–$C_{12}$-alkyl, $C_1$–$C_8$-alkoxy, substituents which confer solubility in water, chosen from the group consisting of carboxylate, sulfonate or ammonium radicals;

$R^3$ is $COOR^5$, $COR^5$, $CONR^5R^6$;

$R^5$ and $R^6$ independently of one another are hydrogen, $C_1$–$C_{12}$-alkyl, $C_3$–$C_6$-cycloalkyl, $C_7$–$C_{10}$-bicycloalkyl, phenyl, naphthyl, optionally substituted, and n is from 1 to 3 since these compounds are particularly photostable and also colorless.

Particular preference is given to oligomeric 4,4-diarylbutadiene-1-carboxylates which also carry a cyano group, an alkylcarbonyl or a carboxylate group in the 1-position.

The radicals X are derived from at least m-valent aliphatic or cycloaliphatic alcohols. They generally have from 2 to 10, preferably from 2 to 6 and in particular from 2 to 4, OH groups.

These alcohols can be linear or branched, and their carbon chains can be interrupted by one or more oxygen or sulfur atoms, by imino groups (—NH—) or $C_1$–$C_4$-alkylimino groups.

The group X is preferably derived from the following known polyols:

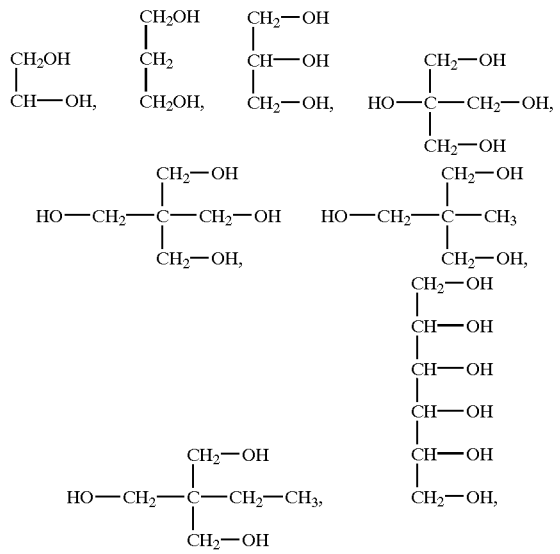

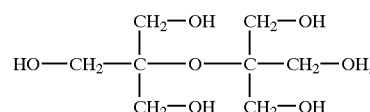
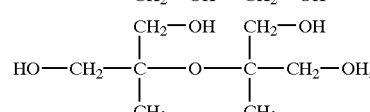
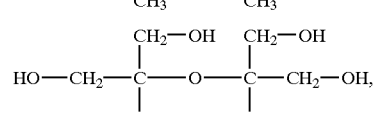
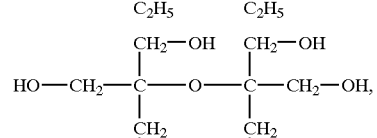
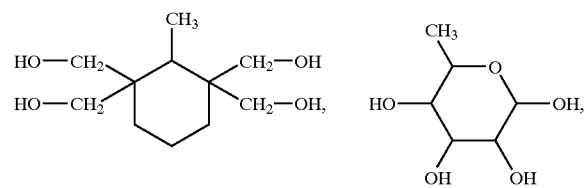
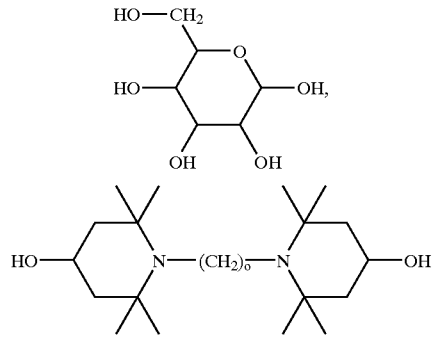

where o has a value from 2 to 8, preferably from 2 to 6, but is particularly preferably 2.

The novel compounds of the formula I are prepared by the Knoevenagel condensation of m mol of aldehydes of the formula III

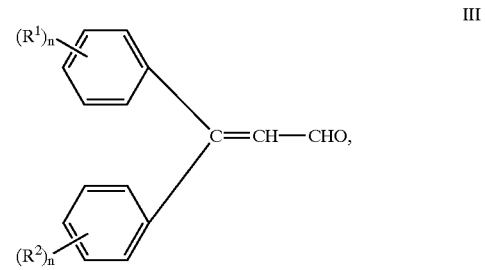

III in which $R^1$, $R^2$ and n are as defined above, with oligomeric, optionally substituted acetic esters of the formula IV

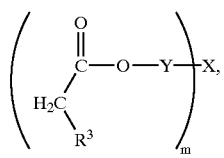

in which $R^3$, Y, X and m are as defined above.

The reaction can be carried out, for example, in aromatic solvents such as toluene or xylene (see, for example, Organikum [Organic Chemistry], 1976 edition, p. 572). Preference is, however, given to polar organic solvents such as dimethylformamide, dimethylacetamide, N-methylpyrrolidone, trialkyl orthoformate or alcohols such as n-propanol, n-butanol, ethylene glycol, diethylene glycol, ethylene glycol monomethyl ether, cyclohexanol or similar compounds. If the starting compounds used already form a liquid mixture, it is possible to dispense with an additional solvent. The reaction temperatures are preferably between 20 and 180° C., particularly preferably between 40 and 150° C. The pressure is preferably normal atmospheric pressure. Depending on the reactivity of the compound IV used, the use of a catalyst or a catalyst mixture is advantageous. Suitable catalysts are, for example, ammonium acetate, piperidine and B-alanine and acetates thereof.

In the case of very long reaction times, it is possible to additionally use, as catalysts for the reaction, Lewis acids such as $AlCl_3$, $ZrCl_4$, $TiCl_4$ or especially $ZnCl_2$ in the amounts customary for this purpose.

The substituted acetic esters IV can be prepared, for example, by reacting, for example, cyanoacetic acid or esters thereof with the corresponding polyols $X(OH)_m$ in the presence of a catalyst such as boric acid, $Na_2CO_3$ or $K_2CO_3$ or tetrabutyl orthotitanate, preferably in toluene or xylene.

The compounds of the formula I according to the invention can in principle be in the form of their various geometric isomers, i.e. with a Z,Z; Z,E; E,Z and/or E,E-configured diene system. Preferred cosmetic sunscreens are the all-E and/or all-Z isomers, and very particularly preferred are the all-E isomers.

The present invention further provides cosmetic and pharmaceutical preparations which comprise from 0.1 to 10% by weight, preferably from 1 to 7% by weight, based on the total amount of the cosmetic and pharmaceutical preparation, of one or more of the compounds of the formula I together with compounds which absorb in the UV-A and UV-B region and which are known per se for cosmetic and pharmaceutical preparations as a sunscreen, the compounds of the formula I generally being used in a smaller amount than the UV-B-absorbing compounds.

The cosmetic and pharmaceutical preparations comprising sunscreens are normally based on a carrier which comprises at least one oil phase. However, preparations based on water alone are also suitable if compounds with hydrophilic substituents are used. Accordingly, suitable preparations are oils, oil-in-water and water-in-oil emulsions, creams and pastes, lip-protection stick compositions or fat-free gels.

Such sunscreen preparations can accordingly be in liquid, paste or solid form, for example as water-in-oil creams, oil-in-water creams and lotions, aerosol foam creams, gels, oils, marking pencils, powders, sprays or alcoholic/aqueous lotions.

Examples of conventional oil components in cosmetics are liquid paraffin, glyceryl stearate, isopropyl myristate, diisopropyl adipate, cetylstearyl 2-ethylhexanoate, hydrogenated polyisobutene, vaseline, caprylic acid/capric acid triglycerides, microcrystalline wax, lanolin and stearic acid.

Examples of conventional cosmetic auxiliaries which may be suitable as additives are coemulsifiers, fats and waxes, stabilizers, thickeners, biogenic active ingredients, film formers, fragrances, dyes, lusterizing agents, preservatives, pigments, electrolytes (e.g. magnesium sulfate) and pH regulators. Suitable coemulsifiers are, preferably, known W/O and also OW emulsifiers, such as polyglycerol esters, sorbitan esters or partially esterified glycerides. Typical examples of fats are glycerides; waxes which may be mentioned include beeswax, paraffin wax or microwaxes, optionally in combination with hydrophilic waxes. Stabilizers which may be used are metal salts of fatty acids, for example magnesium stearate, aluminum stearate and/or zinc stearate. Examples of suitable thickeners are crosslinked polyacrylic acids and derivatives thereof, polysaccharides, in particular xanthan gum, guar guar, agar agar, alginates and tyloses, carboxymethylcellulose and hydroxyethylcellulose, also fatty alcohols, monoglycerides and fatty acids, polyacrylates, polyvinyl alcohol and polyvinylpyrrolidone. Biogenic active ingredients are taken to mean, for example, plant extracts, protein hydrolyzates and vitamin complexes. Examples of traditional film formers are hydrocolloids such as chitosan, microcrystalline chitosan or quaternized chitosan, polyvinylpyrrolidone, vinylpyrrolidone-vinyl acetate copolymers, polymers of the acrylic acid series, quaternary cellulose derivatives and similar compounds. Suitable preservatives are, for example, formaldehyde solution, p-hydroxybenzoate or sorbic acid. Suitable lusterizing agents are, for example, glycol distearic esters, such as ethylene glycol distearate, but also fatty acids and fatty acid monoglycol esters. The dyes which may be used are those substances suitable and approved for cosmetic purposes, such as, for example, those listed in the publication "Kosmetische Färbemittel" from the Farbstoffkommission der Deutschen Forschungsgemeinschaft, published by Verlag Chemie, Weinheim, 1984. These dyes are normally used in concentrations of from 0.001 to 0.1% by weight, based on the total mixture.

The total amount of auxiliaries and additives can be from 1 to 80% by weight, preferably from 6 to 40% by weight, and the nonaqueous content ("active substance") can be from 20 to 80% by weight, preferably from 30 to 70% by weight, based on the formulation. The formulations can be prepared in a manner known per se, i.e. for example by hot, cold, hot/cold or PIT emulsification. This is purely a mechanical process and there is no chemical reaction.

Finally, it is possible additionally to use further substances known per se which absorb in the UV region, provided they are stable in the overall system of the combination of UV filters to be used according to the invention.

Most of the sunscreens in the cosmetic and pharmaceutical preparations which are used for protecting the human epidermis consist of compounds which absorb UV light in the UV-B region, i.e. in the region from 280 to 320 nm. The amount of UV-A absorber to be used according to the invention is, for example, from 10 to 90% by weight, preferably from 20 to 50% by weight, based on the total amount of substances which absorb UV-B and UV-A.

Any UV-A and UV-B filter substances are suitable as UV filter substances which are used in combination with the compounds of the formula I to be used according to the invention. Examples wich may be mentioned are:

| No. | Substance | CAS No. (=acid) |
|---|---|---|
| 1 | 4-Aminobenzoic acid | 150-13-0 |
| 2 | 3-(4-Trimethylammonio)benzylidenebornan-2-one methylsulfate | 52793-97-2 |
| 3 | 3,3,5-Trimethylcyclohexyl salicylate (homosalate) | 118-56-9 |
| 4 | 2-Hydroxy-4-methoxybenzophenone (oxybenzone) | 131-57-7 |
| 5 | 2-Phenylbenzimidazole-5-sulfonic acid and its potassium, sodium and triethanolamine salts | 27503-81-7 |
| 6 | 3,3'-(1,4-Phenylenedimethine)bis(7,7-dimethyl-2-oxobicyclo[2.2.1]heptane-1-methane sulfonic acid) and its salts | 90457-82-2 |
| 7 | Polyethoxyethyl 4-bis(polyethoxy)aminobenzoate | 113010-52-9 |
| 8 | 2-Ethylhexyl 4-dimethylaminobenzoate | 21245-02-3 |
| 9 | 2-Ethylhexyl salicylate | 118-60-5 |
| 10 | Isoamyl 4-methoxycinnamate | 71617-10-2 |
| 11 | 2-Ethylhexyl 4-methoxycinnamate | 5466-77-3 |
| 12 | 2-Hydroxy-4-methoxybenzophenone-5-sulfonic acid (sulisobenzone) and the sodium salt | 4065-45-6 |
| 13 | 3-(4'-Methylbenzylidene)bornan-2-one | 36861-47-9 |
| 14 | 3-Benzylidenebornan-2-one | 15087-24-8 |
| 15 | 1-(4'-Isopropylphenyl)-3-phenylpropane-1,3-dione | 63260-25-9 |
| 16 | 4-Isopropylbenzyl salicylate | 94134-93-7 |
| 17 | 2,4,6-Tri(o-2-ethylhexoxycarbonyl-anilino)-1,3,5-triazine | 88122-99-0 |
| 18 | 3-(4-Imidazolyl)acrylic acid and its ethyl ester | 104-98-3 |
| 19 | Ethyl 2-cyano-3,3-diphenylacrylate | 5232-99-5 |
| 20 | 2-Ethylhexyl 2-cyano-3,3-diphenylacrylate | 6197-30-4 |
| 21 | Menthyl o-aminobenzoate or: 5-methyl-2-(1-methylethyl) 2-aminobenzoate | 134-09-8 |
| 22 | Glyceryl p-aminobenzoate or: 4-aminobenzoic acid 1-glyceryl ester | 136-44-7 |
| 23 | 2,2'-Dihydroxy-4-methoxybenzophenone (dioxybenzone) | 131-53-3 |
| 24 | 2-Hydroxy-4-methoxy-4-methylbenzophenone (mexenone) | 1641-17-4 |
| 25 | Triethanolamine salicylate | 2174-16-5 |
| 26 | Dimethoxyphenylglyoxalic acid or: sodium 3,4-dimethoxyphenylglyoxalate | 4732-70-1 |
| 27 | 3-(4'-Sulfobenzylidene)bornan-2-one and its salts | 56039-58-8 |
| 28 | 4-tert-Butyl-4'-methoxydibenzoylmethane | 70356-09-1 |
| 29 | 2,2',4,4'-Tetrahydroxybenzophenone | 131-55-5 |
| 30 | Dimethicone diethylbenzalmalonate | 207574-74-1 |
| 31 | bis[2-Hydroxy-5-tert-octyl-3-(benzotriazol-2-yl)phenyl]methane (bisoctyltriazone) | 103597-45-1 |
| 32 | 1H-Benzimidazole-4,6-disulfonic acid, 2,2'-(1,4-phenylene)bis-, disodium salt (benzimidazylate) | 180898-37-7 |
| 33 | Phenol, 2,2'-[6-(4-methoxyphenyl)-1,3,5-triazine-2,4-diyl]bis[5-(2-ethylhexyl)oxy] (aniso triazine) | 187393-00-6 |

Finally, micronized pigments such as titanium dioxide and zinc oxide can also be mentioned.

To protect human hair against UV rays, the novel sunscreens of the formula I can be incorporated into shampoos, lotions, gels, hairsprays, aerosol foam creams or emulsions in concentrations of from 0.1 to 10% by weight, preferably from 1 to 7% by weight. The formulations in each case can be used inter alia for washing, coloring and for styling the hair.

The compounds to be used according to the invention are usually notable for a particularly high absorptive power in the UV-A radiation range with sharp band structure. Furthermore, they are readily soluble in cosmetic oils and can be incorporated easily into cosmetic formulations. The emulsions prepared using the compounds I are particularly notable for high stability, the compounds I themselves for high photostability, and the preparations prepared using I for their pleasant feel on the skin.

The UV filter action of the novel compounds of the formula I can also be utilized for stabilizing active ingredients and auxiliaries in cosmetic and pharmaceutical formulations.

The compounds according to the invention are also highly suitable for stabilizing organic materials against the effects of light, oxygen and heat.

Examples of polymers which can be stabilized using the novel compounds I are:

polymers of mono- and diolefins, for example low-density polyethylene or high-density polyethylene, polypropylene, linear polybut-1-ene, polyisoprene, polybutadiene and copolymers of mono- or diolefins or mixtures of said polymers;

copolymers of mono- or diolefins with other vinyl monomers, for example ethylene-alkyl acrylate copolymers, ethylene-alkyl methacrylate copolymers, ethylene-vinyl acetate copolymers or ethylene-acrylic acid copolymers;

polystyrene and copolymers of styrene or a-methyl styrene with dienes and/or acrylic derivatives, for example styrene-butadiene, styrene-acrylonitrile (SAN), styrene-ethyl methacrylate, styrene-butadiene-ethyl acrylate, styrene-acrylonitrile-methacrylate, acrylonitrile-butadiene-styrene (ABS) or methyl methacrylate-butadiene-styrene (MBS);

halogen-containing polymers, for example polyvinyl chloride, polyvinyl fluoride, polyvinylidene fluoride and copolymers thereof;

polymers derived from α,β-unsaturated acids and derivatives thereof, such as polyacrylates, polymethacrylates, polyacrylamides and polyacrylonitriles;

polymers derived from unsaturated alcohols and amines or from their acrylic derivatives or acetals, for example polyvinyl alcohol and polyvinyl acetate;

polyurethanes, polyamides, polyureas, polyphenylene ethers, polyesters, polycarbonates, polyoxymethylenes, polysulfones, polyether sulfones and polyether ketones.

Furthermore, the novel compounds I can be used to stabilize surface coatings, e.g. industrial finishes. Of these, baking finishes are emphasized in particular, and of these in turn automotive finishes, preferably two-coat finishes.

The novel compounds I can be added to the coating in solid or dissolved form. Their good solubility in coating systems is particularly advantageous.

The novel compounds I are preferably used for stabilizing polyolefins, in particular polyethylene, polycarbonates, polyamides, polyesters, polystyrene, ABS and polyurethanes. In particular, it is also possible to stabilize films of said polymers.

For these areas of application, the compounds are used in concentrations of from 0.01 to 5% by weight, based on the amount of polymer, preferably in a concentration of from 0.02 to 2% by weight. The combination with other stabilizers, for example antioxidants, metal deactivators or other sunscreens and also with antistatic or flame-inhibiting agents, is often advantageous. Particularly important costabilizers are, for example, sterically hindered phenols and phosphites, phosphonites, amines and sulfur compounds.

Examples of suitable costabilizers are:
phenolic antioxidants such as
2,6-di-tert-butyl-4-methylphenol,
n-octadecyl-β-(3,5-di-tert-butyl-4-hydroxyphenol) propionate,
1,1,3-tris(2-methyl-4-hydroxy-5-tert-butylphenyl)butane,
1,3,5-trimethyl-2,4,6-tris(3,5-di-tert-butyl-4-hydroxybenzyl)-benzene, 1,3,5-tris(3,5-di-tert-butyl-4-hydroxybenzyl)isocyanurate,
1,3,5-tris[β-(3,5-di-tert-butyl-4-hydroxyphenyl)propionylethyl]isocyanurate,
1,3,5-tris(2,6-dimethyl-3-hydroxy-4-tert-butylbenzyl)isocyanurate and
pentaerythritol tetrakis[β-(3,5-di-tert-butyl-4-hydroxy)propionate], phosphorus-containing antioxidants such as
tris(nonylphenyl)phosphite, distearylpentaerythritol phosphite,
tris(2,4-di-tert-butylphenyl)phosphite,
tris(2-tert-butyl-4-methylphenyl)phosphite,
bis(2,4-di-tert-butylphenyl)pentaerythritol diphosphite and
tetrakis(2,4-di-tert-butylphenyl)-4,4'-biphenylene diphosphite, sulfur-containing antioxidants such as
dilauryl thiodipropionate,
dimyristyl thiodipropionate,
distearyl thiodipropionate,
pentaerythritol tetrakis(β-laurylthiopropionate) and
pentaerythritol tetrakis(β-hexylthiopropionate), sterically hindered amines such as
bis(2,2,6,6-tetramethylpiperidyl)sebacate,
bis(1,2,2,6,6-pentamethylpiperidyl)sebacate,
bis(1,2,2,6,6-pentamethylpiperidyl)ester,
N,N'-bis(formyl)-bis(2,2,6,6-tetramethyl-4-piperidyl)-1,6-hexane-diamine, the condensation product of
1-hydroxy-2,2,6,6-tetramethyl-4-hydroxypiperidine and succinic acid, the condensation product of
N,N'-(2,2,6,6-tetramethylpiperidyl)hexamethylenediamine and 4-tert-octylamino-2,6-dichloro-1,3,5-s-triazine,
poly[3-(eicosyl/tetracosyl)-1-(2,2,6,6-tetramethylpiperidin-4-yl)pyrrolidine-2,5-dione],
tris(2,2,6,6-tetramethylpiperidyl)nitrilotriacetate,
tetrakis(2,2,6,6-tetramethyl-4-piperidyl)-1,2,3,4-butanetetra-carboxylic acid,
1,1'-(1,2-ethanediyl)-bis-(3,3,5,5-tetramethylpiperazinone), the condensation products of
4-amino-2,2,6,6-tetramethylpiperidines and tetramethylolacetylenediureas, and also
2-(2'-hydroxyphenyl)benzotriazoles,
2-hydroxybenzophenones,
aryl esters of hydroxybenzoic acids,
α-cyanocinnamic acid derivatives,
nickel compounds or
oxalic dianilides.

For mixing the novel compounds I, especially with polymers, it is possible to use all known equipment and methods for incorporating stabilizing agents or other additives into polymers.

The novel oligomeric 4,4-diarylbutadienecarboxylates and -carboxamides are notable for good compatibility with customary types of polymers and for good solubility and excellent compatibility in customary coating systems. Usually, they have no or only a very slight intrinsic color, are stable and nonvolatile at the customary polymer and coating processing temperatures and afford a long protective period for the materials coated therewith. In particular, however, they display virtually no tendency toward migration in polymers.

EXAMPLES

Example 1

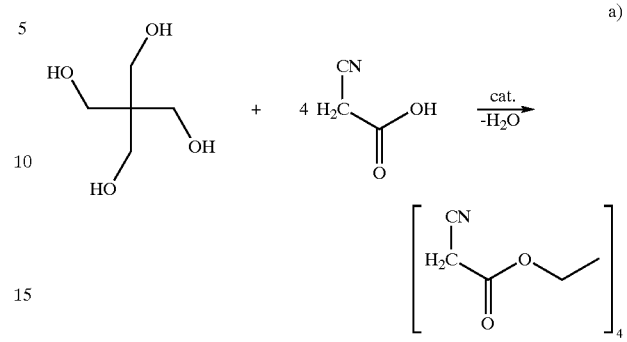

a)

0.1 mol of cyanoacetic acid was suspended with 0.025 mol of pentaerythritol in 200 ml of xylene. 2 g of para-toluenesulfonic acid were added and the mixture was heated to boiling with reflux condensation, the water of reaction which formed being removed at the water separator. After the mixture had been cooled to room temperature, the product was separated off by filtration, washed twice with water and dried under reduced pressure (200 mbar) at 50° C.
Yield: 80% of theory.

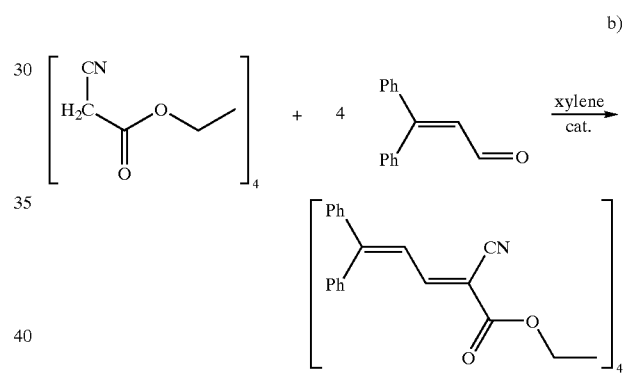

b)

0.05 mol of the compound from 1 a) were suspended with 0.2 mol of β-phenylcinnamaldehyde in 150 ml of xylene. After 2 ml of piperidine and 2 ml of glacial acetic acid had been added, the mixture was heated to boiling with reflux condensation. The reaction was complete after about 6 h (TLC check). The product was filtered off with suction and recrystallized from xylene.
Yield: 70% of theory.
$\lambda_{max}$: 352; $E_1^1$: 810

Example 2

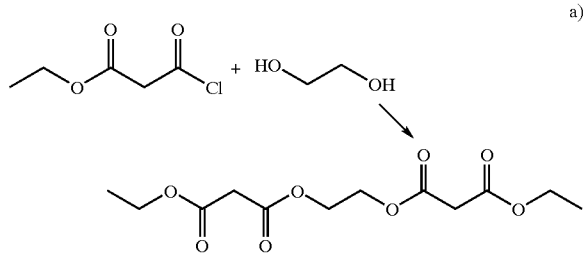

a)

0.0475 mol of ethylene glycol and 0.1 mol of triethylamine were dissolved in 100 ml of toluene. 0.1 mol of ethyl malonyl chloride was carefully added to this solution at from 15 to 20° C., and the mixture was then stirred at room temperature for 2 h. 200 ml of water were added and the phases were separated. The organic phase was washed with 2×150 ml of water and once with saturated $NaHCO_3$ solution. The product was then dried over $Na_2SO_4$ and concentrated by evaporation to give a pale yellow oil.

Yield 58% of theory.

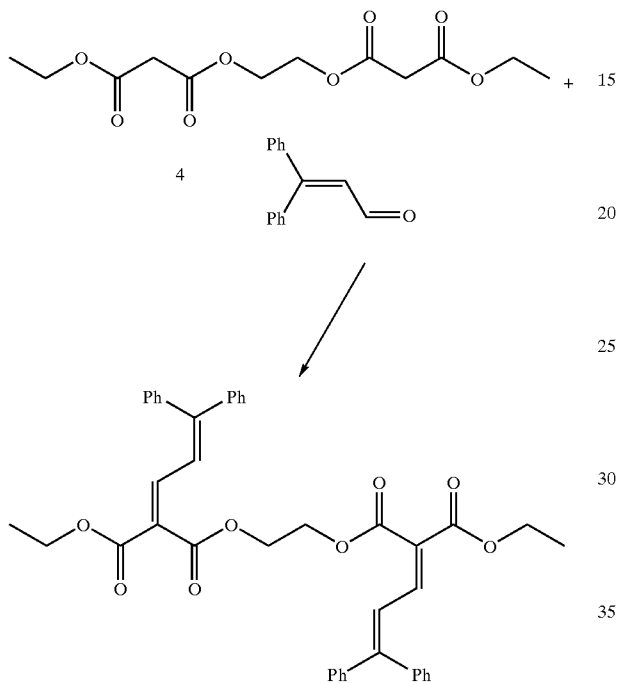

0.025 mol of the compound from 2 a) and 0.05 mol of β-phenylcinnamaldehyde were dissolved in 100 ml of ethanol. 2 ml of piperidine and 2 ml of glacial acetic acid were added. The mixture was then boiled for 5 h with reflux condensation, water was added and the oil which separated out was separated off. The aqueous phase was extracted with methylene chloride, and the combined organic phases were dried over $Na_2SO_4$ and concentrated by evaporation.

Yield 60% of theory; yellow viscous oil $\lambda_{max}$: 336; $E_1^1$: 800

Example 3

The compound of the formula $\lambda_{max}$: 354; $E_1^1$: 850 was prepared in the same manner as described in Example 1.

Example 4

(Cosmetic Preparation)
Sun cream (SPF 20)
mass content
(% by weight)

| ad 100 | water |
|---|---|
| 8.00 | octyl methoxycinnamate |
| 8.00 | titanium dioxide |
| 6.00 | PEG-7 hydrogenated castor oil |
| 5.00 | compound of Example 1 |
| 6.00 | mineral oil |
| 5.00 | zinc oxide |
| 5.00 | isopropyl palmitate |
| 5.00 | imidazolidinyl urea |
| 3.00 | jojoba oil |
| 2.00 | PEG-45/dodecyl glycol copolymer |
| 1.00 | 4-methylbenzylidene camphor |
| 0.60 | magnesium stearate |
| 0.50 | tocopheryl acetate |
| 0.25 | methylparaben |
| 0.20 | disodium EDTA |
| 0.15 | propylparaben |

We claim:
1. An oligomeric 4,4-diarylbutadienecarboxylate or -carboxamide of the formula I in which
$R^1$ and $R^2$ independently of one another are hydrogen, an aliphatic, cycloaliphatic, aromatic, araliphatic or heterocyclic radical or substituents which confer solubility in water, chosen from the group consisting of carboxylate, sulfonate or ammonium radicals;
$R^3$ is an aliphatic, cycloaliphatic, aromatic, araliphatic or heterocyclic radical or a radical which is bonded by a carbonyl, sulfonyl or a phosphonyl group, or is a carboxylate or a cyano group;
Y is the group —O—    or    —N—
                   |
                   $R^4$ in which
$R^4$ is hydrogen, an aliphatic, cycloaliphatic, aromatic, araliphatic or heterocyclic radical and
m is from 2 to 10,
n is from 1 to 3, and
X is the m-valent radical of a polyol having from 2 to 10 hydroxyl groups.
2. An oligomeric 4,4-diarylbutadienecarboxylate or -carboxamide of the formula I as claimed in claim 1, wherein the variables independently of one another are defined as follows:
$R^1$ and $R^2$ are hydrogen, $C_1$–$C_{20}$-alkyl, $C_2$–$C_{10}$-alkenyl, $C_3$–$C_{10}$-cycloalkyl, $C_3$–$C_{10}$-cycloalkenyl, $C_1$–$C_{12}$- alkoxy, $C_1$–$C_{20}$-alkoxycarbonyl, $C_1$–$C_{12}$-alkylamino, $C_1$–$C_{12}$-dialkylamino, aryl, heteroaryl, optionally substituted, substituents which confer solubility in water, chosen from the group consisting of carboxylate, sulfonate or ammonium radicals;

$R^3$ is hydrogen, $COOR^5$, $COR^5$, $CONR^5R^6$, CN, O=S(—$R^5$)=O, O=S(—$OR^5$)=O, $R^7$O—P(—$OR^8$)=O, $C_1$–$C_{20}$-alkyl, $C_2$–$C_{10}$-alkenyl, $C_3$–$C_{10}$-cycloalkyl, $C_7$–$C_{10}$-bicycloalkyl, $C_3$–$C_{10}$-cycloalkenyl, $C_7$–$C_{10}$-bicycloalkenyl, aryl, heteroaryl, optionally substituted;

$R^4$ to $R^8$ are hydrogen, $C_1$–$C_{20}$-alkyl, $C_2$–$C_{10}$-alkenyl, $C_3$–$C_{10}$-cycloalkyl, $C_7$–$C_{10}$-bicycloalkyl, $C_3$–$C_{10}$-cycloalkenyl, $C_7$–$C_{10}$-bicycloalkenyl, aryl, heteroaryl, each optionally substituted;

it being possible for the variables $R^5$ to $R^8$ to form with each other, in each case together with the atoms to which they are bonded, a common 5- or 6-membered ring.

3. An oligomeric 4,4-diarylbutadienecarboxylate or -carboxamide of the formula I as claimed in claim 1, wherein X is an ethylene radical.

4. An oligomeric 4,4-diarylbutadienecarboxylate or -carboxamide of the formula I as claimed in claim 1, wherein X is the pentaerythritol radical of the formula II

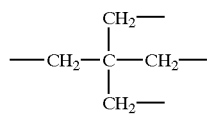

II

5. A cosmetic or pharmaceutical preparation comprising a sunscreen for protecting the human epidermis or human hair against UV light in the range from 280 to 400 nm, which comprises, in a cosmetically and pharmaceutically suitable carrier, alone or together with compounds which absorb in the UV region and which are known per se for cosmetic and pharmaceutical preparations, an effective amount of a compound of the formula I as claimed in claim 1 as a photostable UV filter.

6. A process for the preparation of compounds of the formula I as claimed in claim 1, which comprises reacting oligomeric, optionally substituted acetic esters of the formula IV

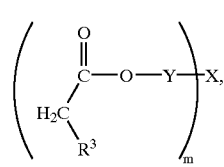

IV with m mol of compounds of the formula III

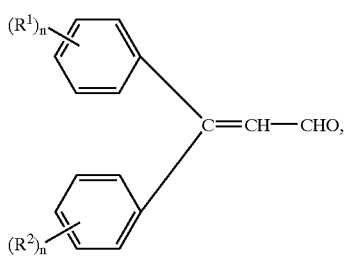

III in which $R^1$, $R^2$, $R^3$, X, Y, m and n are as defined in claim 1.

* * * * *